US008217203B2

(12) United States Patent
Bonrath et al.

(10) Patent No.: US 8,217,203 B2
(45) Date of Patent: Jul. 10, 2012

(54) PROCESS FOR THE PREPARATION OF (E, E)-FARNESYL ACETONE

(75) Inventors: Werner Bonrath, Freiburg (DE); Rolf Kuenzi, Basel (CH)

(73) Assignee: DSM IP Assets B.V., Heerlen (NL)

( * ) Notice: Subject to any disclaimer, the term of this patent is extended or adjusted under 35 U.S.C. 154(b) by 0 days.

(21) Appl. No.: 12/672,276

(22) PCT Filed: Jul. 22, 2008

(86) PCT No.: PCT/EP2008/059601
§ 371 (c)(1),
(2), (4) Date: Feb. 5, 2010

(87) PCT Pub. No.: WO2009/019132
PCT Pub. Date: Feb. 12, 2009

(65) Prior Publication Data
US 2010/0204520 A1      Aug. 12, 2010

(30) Foreign Application Priority Data

Aug. 8, 2007   (EP) .................................. 07015579

(51) Int. Cl.
*C07C 49/29*    (2006.01)
*C07C 49/203*   (2006.01)

(52) U.S. Cl. .................. 568/391; 568/403; 568/417
(58) Field of Classification Search .................. 568/391, 568/403, 417
See application file for complete search history.

(56) References Cited

U.S. PATENT DOCUMENTS 6,034,279 A * 3/2000 Kashammer et al. ......... 568/391

FOREIGN PATENT DOCUMENTS

| CN | 1 651 382 | 8/2005 |
|---|---|---|
| DE | 11 93 490 | 5/1965 |
| DE | 196 49 564 | 6/1998 |

OTHER PUBLICATIONS

International Search Report for PCT/EP2008/059601, mailed Dec. 19, 2008.
Saucy, G. et al., "Über die reaction von tertiären Vinylcarbinolen mit Isopropenyläther, Eine neue Methode zur Herstellung von gamma, delta-ungesattigten Ketonen", Helv. Chim. Acta, vol. 50, No. 218, (1967), pp. 2091-2095.

* cited by examiner

*Primary Examiner* — Sikarl Witherspoon
(74) *Attorney, Agent, or Firm* — Nixon & Vanderhye P.C.

(57) ABSTRACT

A process for the preparation of E-farnesyl acetone characterized by reaction of nerolidol with isopropenylmethyl ether in the presence of an acidic catalyst at elevated temperature and isolation by fractionated distillation.

8 Claims, No Drawings

PROCESS FOR THE PREPARATION OF (E, E)-FARNESYL ACETONE

This application is the U.S. national phase of International Application No. PCT/EP2008/059601 filed 22 Jul. 2008, which designated the U.S. and claims priority to Europe Application No. 07015579.1 filed 8 Aug. 2007, the entire contents of each of which are hereby incorporated by reference.

The present invention relates to a process for the preparation of E/E-farnesyl acetone (2,6,10-trimethyl-2,6,10-pentadecatrien-14-one) which is an interesting compound for the flavor and fragrance industry and an intermediate for pharmaceutically and nutritionally interesting compounds, e.g., β-zeacarotene.

CH 260 081 describes the preparation of farnesyl acetone by transformation of nerolidol into its acetylacetate with diketene in the presence of NaOEt at 0-5° C., decarboxylation at a pressure of 5 mm and a temperatre of 190-200° C. and rectification at 2.5 mm (yield 45.7 w %). Alternatively, Me-acetoacetate and nerolidol are heated during 10 hours in the presence of dry $K_2CO_3$ at 150-160° C. After addition of further $K_2CO_3$ the mixture is heated again for 10 hours at this temperature under removal of water, alcohol and acetone. By fractionated distillation of the residue farnesyl acetone is obtained in a yield of 60 w %.

Treatment of nerolidol with $PBr_3$ in ether at −18° C. to farnesylbromide, condensation with sodium acetoacetic ester giving Et-farnesyl acetoacetate and ketone cleavage with aqueous $Ba(OH)_2$ yielding farnesyl acetone and farnesyl acetic acid is described by A. Caliezi et al. (Helv. Chim. Acta 35, 1649-55 [1952]).

According to I. N. Nazarov et al. (Izvestiya Akademii nauk SSSR, Seriya Khimicheskaya 1957, 1267-70; Chem. Abstr. 52:34658 [1958]) the transformation of tertiary vinyl alcohols, e.g., nerolidol, into unsaturated ketones can be achieved by 3 procedures: (1) treatment with a hydrogenhalide HX to form an allyl halide which is treated with sodium acetoacetic ester; (2) treatment of the alcohol with acetoacetic ester at 140-190° C. or (3) treatment of the alcohol with diketene. Best results were obtained by method (3) which gave unsaturated ketones in 60-65 w % yields.

The disadvantages of these methods are formation of waste, particularly salts, low yields and low stereo-specificity. A more convenient synthesis of γ, δ-unsaturated carbonyl compounds, e.g., farnesyl acetone from tertiary vinyl carbinols, e.g., nerolidol and isopropenylmethyl ether (IPM) under pressure (6 added atm. $N_2$), at 125° C. for 16 hours under acidic conditions (phosphoric acid or p-toluenesulfonic acid) is disclosed in DE 1 193 490 and by Saucy and Marbet in Helv. Chim. Acta 50, 2091-2095 (1967).

J. Zhang et al. (Huaxue Shijie 45, 86-88 (2004); Chem. Abstr. 146:296095 (2006)) synthesized farnesyl acetone in yields of up to 50.9 w % from linalool by Carroll rearrangement, Grignard reaction and catalytic hydrogenation. This is a relatively extravagant procedure which is not very economic in view of waste and low yield involved.

While four stereo-isomers of farnesyl acetone exist (E/E, E/Z, Z/E, Z/Z) none of the references above gives any information on the steric nature of the final product. Nowhere the stereospecific preparation of E/E-farnesyl acetone is disclosed. Differences in the steric nature of farnesyl acetone are of importance with respect to the use of the isomers in the flavor and fragrance industry. The task of the present invention was to find a stereo-specific economic synthesis of E/E-farnesyl acetone in high yield at an industrial scale of at least several t/a.

This has been achieved by reacting nerolidol with isopropenylmethyl ether (IPM) in the presence of an acidic catalyst and isolating pure E/E-farnesyl acetone from the reaction mixture by fractionated distillation. The present invention, therefore, relates to a process for the preparation of E/E-farnesyl acetone by reacting nerolidol with IPM in the presence of an acidic catalyst and isolating it by fractionated distillation. Thus, E/E-farnesyl acetone can be obtained in a steric purity of at least 90%.

The invention also relates to E/E-farnesyl acetone thus obtained/obtainable and to the use of E/E-farnesyl acetone obtained/obtainable according to the method of the present invention as a flavor or fragrance ingredient, especially in perfumes in their broadest sense, and an intermediate in the preparation of carotenoids.

The starting materials, E/Z-nerolidol or E-nerolidol and isopropenylmethyl ether, are commercially available products. E-Nerolidol can also be obtained from commercially available E/Z-nerolidol by fractionated distillation.

The acidic catalyst is preferably phosphoric acid, suitably in an amount of 0.01 to 0.5, preferably 0.2 mol % relative to nerolidol in the reaction mixture. It is advantageous to use the phosphoric acid not as such but in a suitable organic solvent, such as acetone, preferably in a concentration of 10-30 w %. However, other mineral acids, such as sulfuric acid, and strong organic acids such as p-toluenesulfonic acid, methanesulfonic acid, tri-chloroacetic acid or oxalic acid, can also be used, however, less favorably.

The reaction is suitably carried out at a temperature in the range of 100-200° C. for 8 to 20 hours, preferably at 120-180° C., more preferably at 140-160° C. for about 16 hours total reaction time.

The reaction can be carried out under atmospheric pressure and reflux or under overpressure in a closed reactor, if desired under an inert atmosphere, e.g., nitrogen. Furthermore, the reaction is carried out with an excess of IPM in the molar range of 2.5-5.0, preferably more than 3.8:1 mole of nerolidol. The end of the reaction can be determined as usual by taking samples and analyzing them by gas chromatography.

From the reaction mixture the desired E/E-farnesyl acetone is isolated by fractionated distillation under reduced pressure, preferably at less than 0.1 mbar, more preferably at 0.03-0.02 mbar, as main fraction. Advantageously the acidic catalyst is neutralized by addition of a basic organic or inorganic compound, e.g., sodium acetate, and, if desired, removed as well as the low-boiling components before fractionation.

It was found that phosphoric acid catalyzed $C_3$-elongation of E/Z-nerolidol resulted in a mixture of the following four isomers of farnesyl acetone (FA) at a 89-91% yield of all isomers after distillation (separation from low- and high-boilers): E/E-FA: 34%; (5Z,9E)-FA+(5E,9Z)-FA: 49% (the two isomers cannot be separated by gas chromatography); Z/Z-FA: 17%. The corresponding $C_3$-elongation of E-nerolidol resulted in a mixture of the two isomers E/E-FA and (5Z,9E)-FA of ca. 60:40% at a 86-88% yield of total isomers after distillation (separation from low- and high-boilers).

The invention is illustrated in more detail by the following Examples.

EXAMPLE 1

Phosphoric Acid Catalyzed Preparation of E/E-Farnesyl Acetone from E-Nerolidol A 1.0 liter stainless steel batch reactor (Medimex-High Pressure) with electrical heating and water cooling system in the jacket, a pressure sensor and stainless steel propeller was loaded with a mixture of 1.2885 g of a solution of 18 w % $H_3PO_4$ in acetone (2.37 mMol, 0.3 Mol %) and 179.5 g of E-nerolidol (0.790 Mol). 225 g of isopropenylmethyl ether (IPM, 3.01 Mol, 3.81 equivalent) were added. Under stirring (500 rpm) the mixture was heated to 160° C. within two hours. After 16 hours total reaction time the reaction mixture was cooled to 25° C., drawn from the reactor under reduced pressure and stirred with 2 g of sodium acetate for 30 minutes. After filtration over a 5 μm Teflon membrane the low-boilers were removed in two steps (at 10 mbar and 0.05 mbar on pump) in a Rota vapor at 40° C. The crude product (yield 93.1%, selectivity 0.94) was distilled in a 500 ml two-necked round-bottomed flask with PT 100, magnetic stirrer, Liebig condenser, Anschütz Thiele separator, cold trap and high-vacuum pump in an oil bath. At a bath temperature of 140° C., an inner temperature of 125-127° C., a head temperature of 118-122° C. and an absolute pressure of 0.03-0.02 mbar (on the pump) a mixture of E/E- and (5Z,9E)-farnesyl acetone was obtained in a yield of 86%. A pre-fraction with a mixture of E/E- and (5Z,9E)-farnesyl acetone was obtained in a yield of 3.7% at 67-140° C., 44.5-123° C., 27.3-111° C., respectively, and 0.03 mbar (on pump). Total yield of the main- and pre-fraction 89.7%, selectivity 0.9). The E/E-farnesyl acetone was separated from the (5Z/9E)-farnesyl acetone by distillation. The product was characterized by $^1H$ and $^{13}C$-NMR spectroscopy. The purity was determined by gas chromatography.

E/E-FA 300 MHz $^{13}C$-NMR ($CDCl_3$): δ (ppm, TMS)= 208.8, 136.4, 135.0, 131.3, 124.4, 124.0, 122.5, 43.8, 39.7, 39.6, 29.9, 26.8, 26.5, 25.5, 22.5, 17.7, 16.0 (2C).

EXAMPLE 2

In the same manner as described in Example 1 starting from 199 g E-nerolidol, 1.38 g catalyst solution and 3.15 equivalents of IPM there was obtained a mixture of E/E- and (5Z,9E)-farnesyl acetone in a yield of 89.8%, selectivity 0.90 (crude) and of 87.4% (Total of main- and pre-fraction, after separation of the low- and high-boilers) with a selectivity of 0.87.

EXAMPLE 3

In the same manner as described in Example 1 staring from 224.4 g E-nerolidol, 1.56 g of catalyst solution and 2.5 equivalents of IPM there was obtained a mixture of E/E- and (5Z,9E)-farnesyl acetone in a yield of 88.2%, selectivity 0.88 (crude) and of 86.1% (Total of main- and pre-fraction, after separation of the low- and high-boilers) with a selectivity of 0.86.

The invention claimed is:

1. A process for the preparation of E/E-farnesyl acetone in a steric purity of at least 90% which comprises reacting E-nerolidol with isopropenylmethyl ether in a molar amount in the range of 1:3.5-5.0 and in the presence of phosphoric acid as catalyst in an amount of 0.01 to 0.5 mol % relative to nerolidol at elevated temperature of 100 to 200° C. for 8 to 20 hours, and isolating E/E-farnesyl acetone by fractionated distillation.

2. The process of claim 1, wherein isopropenylmethyl ether is reacted with E-nerolidol in a molar excess amount of more than 3.8 moles isopropenylmethyl ether to 1 mole E-nerolidol.

3. The process of claim 1, wherein the phosphoric acid is in an acetonic solution.

4. The process of claim 1, wherein pure E/E-farnesyl acetone in a steric purity of at least 90% is obtained by fractionated distillation of the reaction mixture under an absolute pressure of less than 0.1 mbar.

5. A process for the preparation of E/E-farnesyl acetone in a steric purity of at least 90% which comprises reacting E-nerolidol with isopropenylmethyl ether in a molar amount in the range of 1:2.5-5.0 and in the presence of phosphoric acid catalyst at elevated temperature, and isolating E/E-farnesyl acetone by fractionated distillation.

6. The process of claim 5, wherein the phosphoric acid catalyst is present in an amount of 0.01 to 0.5 mol % relative to the E-nerolidol.

7. The process of claim 6, wherein the phosphoric acid catalyst comprises phosphoric acid in an acetone solvent.

8. The process of claim 7, wherein the phosphoric acid catalyst is present in the acetone solvent in a concentration of 10-30 w %.

* * * * *